US008751266B2

(12) United States Patent
Stang

(10) Patent No.: US 8,751,266 B2
(45) Date of Patent: Jun. 10, 2014

(54) METHOD AND SYSTEM FOR FACILITATING CLINICAL DECISIONS

(75) Inventor: Paul Stang, Blue Bell, PA (US)

(73) Assignee: Cerner Innovation, Inc., Overland Park, KS (US)

( * ) Notice: Subject to any disclaimer, the term of this patent is extended or adjusted under 35 U.S.C. 154(b) by 1599 days.

(21) Appl. No.: 11/366,804

(22) Filed: Mar. 3, 2006

(65) Prior Publication Data

US 2006/0206359 A1 Sep. 14, 2006

Related U.S. Application Data

(60) Provisional application No. 60/658,152, filed on Mar. 4, 2005.

(51) Int. Cl.
 *G06Q 50/00* (2012.01)
(52) U.S. Cl.
 USPC .................................. 705/3; 705/2; 707/600
(58) Field of Classification Search
 USPC .......................................... 705/2–4; 707/600
 See application file for complete search history.

(56) References Cited

U.S. PATENT DOCUMENTS

| 6,063,028 | A | * | 5/2000 | Luciano | 600/300 |
| 6,108,635 | A | * | 8/2000 | Herren et al. | 705/2 |
| 6,322,504 | B1 | * | 11/2001 | Kirshner | 600/300 |
| 6,576,471 | B2 | * | 6/2003 | Otvos | 436/71 |
| 6,584,445 | B2 | * | 6/2003 | Papageorge | 705/3 |
| 2001/0039503 | A1 | * | 11/2001 | Chan et al. | 705/2 |
| 2003/0233250 | A1 | * | 12/2003 | Joffe et al. | 705/2 |
| 2004/0044546 | A1 | * | 3/2004 | Moore | 705/2 |

OTHER PUBLICATIONS

Stegmayr at al. titled "Stroke Incidence and Mortality Correlated to Stroke Risk Factors in the Who Monica Project" (Stroke. 1997; 28:1367-74), hereinafter Stroke.*
McAlister, F. "Applying the results of systematic reviews at the bedside." Systematic Reviews in Health Care: Meta-Analysis in Context, 2nd Ed. Ed. Egger, M. et al. Boston, MA: BMJ Books 2001. 373-85, hereinafter McAlister.*

* cited by examiner

*Primary Examiner* — Mark Holcomb
(74) *Attorney, Agent, or Firm* — Shook, Hardy & Bacon L.L.P.

(57) ABSTRACT

A method and system for providing information for facilitating health care and clinical decisions. The method includes receiving input data specifying patient information, comparing that data with one or more predetermined sets of reference data, and determining and displaying the output data. The output data can be displayed graphically, such as using bubbles of different color and size, to indicate risk factors and their contribution to potential health problems. After displaying the data, a second set of input data can be entered, and this data is compared to the first set of data and to one or more sets of reference data. A second set of output data is generatable and displayable alongside the first set of output data.

23 Claims, 8 Drawing Sheets

Communication Network System
30

FIG. 4

METHOD AND SYSTEM FOR FACILITATING CLINICAL DECISIONS

CROSS-REFERENCE TO RELATED APPLICATIONS

The present application claims priority from U.S. Provisional Patent Application Ser. No. 60/658,152, which was filed on Mar. 4, 2005, and is entitled "Method and System for Facilitating Clinical Decisions," the entirety of which is incorporated herein by reference.

BACKGROUND OF THE INVENTION

1. Field of the Invention

The present invention relates to a method and system for facilitating health care decisions related to health issues, and in particular to a method and system for providing information showing the relationship between the risk and the benefit of clinical therapies and/or applications with respect to medical ailments, diseases and/or conditions.

2. Description of the Related Art

As the bio-medical industry advances in their findings and research of various ways to treat or attend to health issues, health care providers, payors, employers, health care delivery systems, regulators, the government, as well as patients, are exposed to an increased amount of clinical applications and regimens, based on various drug therapies, for example. Often times, clinicians are pressed to provide information, education and guidance to their patients in very brief clinical encounters, resulting in patients that are unable to understand the technical language of their clinicians, unable to absorb and retain all the information provided to them, or unable to grasp certain key concepts during these brief encounters. Consequently, patients are not properly educated or informed about the clinical applications or therapies under which they are placed. As a result, very often the patients do not adhere to the application or therapy they have been prescribed to follow or are unable to understand the information with which they have been presented.

Studies have shown that a patient well-informed about the health risks and benefits associated with the patient's therapy has significantly better adherence to the recommended therapies or regimens. In particular, a patient's adherence to a recommended therapy often depends upon the patient having an understanding of the benefits to the patient's health and life span under such recommended therapy, and the potential risks of declining health or shortened life span if the patient were not to follow such recommended therapy. As such, patients are in need of information that can empower them to better adhere to their recommended therapies and regimens.

On the flip side, clinicians are also seeking more efficient ways to communicate concepts to patients in a way that informs and motivates them to take responsibility for their health and adhere to recommended therapies. For example, clinicians often provide medical pamphlets or articles to their patents, but these documents are often discarded or ignored by the patients, which renders them useless. Also, research organizations are constantly struggling to find effective ways of communicating their researched data and studies regarding the benefit and risk of a certain recommended therapy or regimen to all of their key constituencies, such as clinicians, patients, managed health care companies, and regulators, and existing efforts are typically ineffective.

The Internet is generally a source of vast information. However, the endless volumes of information available on the Internet from a variety of sources of varying credibility can deter, rather than encourage the patient to find helpful information. For instance, the large volumes can overwhelm the patient searching for very specific information. Furthermore, the volumes of information available on the Internet are often technically complex and not easily understood by a lay person, such as a patient, or the information may lack consistency or validity from one source to another. Therefore, the information on the Internet is not always helpful to the patient.

While there is some evidence that intensive multi-modal interventions will improve compliance with prescribed courses of therapy, success often varies according to the impact of the medication on the disease symptoms. This has led the World Health Organization, among others, to conclude that there is no single intervention strategy, or even combination of strategies, that has been shown to be effective across all patients, conditions, and settings. As such, there exists a need for methods and systems that provide patient- and condition-specific information during the course of treatment.

Additionally, many patients feel overwhelmed by the amount of information available and the format by which that information is presented. The use of visual information can increase the impact and effectiveness of information production. Visual information provides context, can be processed quickly, and overcomes issues in numeracy and literacy. Further, many people process and retain visually-presented information more efficiently.

Studies have shown that present methods for delivering information to facilitate clinical decisions are insufficient. For example, package inserts refer to side effects in such categories as "very common," "common," "uncommon," "rare," and "very rare," while seemingly straightforward, are misinterpreted by margins of up to 50% of their actual indication of risk level.

In view of the above, there is a need for a method and system for providing information to facilitate clinical decisions, for example, by showing the relationship between the risk and the benefit of any clinical therapies or applications with respect to medical ailments, diseases and conditions. Further, there exists a need for methods and systems of presenting that information visually, providing maximum impact and ease of understanding.

BRIEF SUMMARY OF THE INVENTION

The present invention includes a method and system for providing information to facilitate health care and clinical decisions, the system including a computer system with application software and a communication network. The present invention, in one embodiment, provides a graphical user interface for the entry of data, such as patient risk factors, and patient health changes; and for displaying information, such as in a graphical manner, to show the relationship between risk and benefit with respect to any type of clinical application or therapy. This invention can also display the population exposures and outcomes, costs and benefits, antecedents and outcomes, causes and effects, and comorbidities of any number of health care scenarios. It is a graphical representation of the relationship between events.

In another embodiment of the present invention, the graphical user interface can be configured to provide supplemental information concerning a health or medical subject matter. In an exemplary embodiment, a user can position a cursor on the displayed subject matter, and upon accessing, such as with a click of the mouse, supplemental information in the various formats may be displayed or made available to the user.

Additional advantages and novel features of the invention will be set forth in part in the description that follows, and in part will become more apparent to those skilled in the art upon examination of the following or upon learning by practice of the invention.

BRIEF DESCRIPTION OF THE SEVERAL VIEWS OF THE DRAWINGS

FIG. 4 illustrates an example of the graphic user-interface screen based on example data for a hypothetical patient.

DETAILED DESCRIPTION OF THE INVENTION

Figure 1:
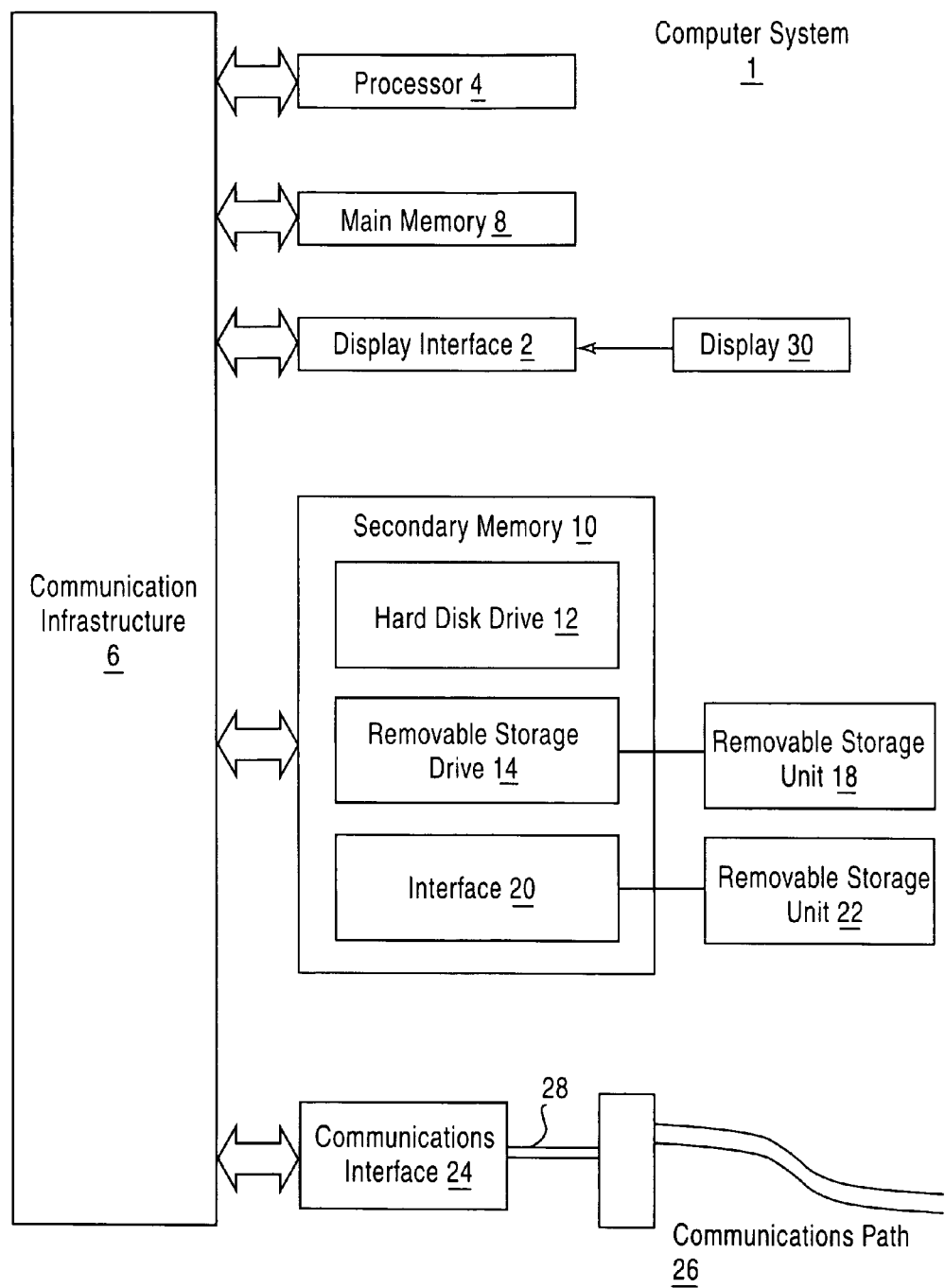
FIG. 1 presents a computer system implementation capable of carrying out the functionality of the current invention.

FIG. 1 illustrates a block diagram with various computer system components for use with an exemplary implementation of a clinical decision system, in accordance with one embodiment of the present invention.

As shown in FIG. 1, the controller of the present invention may be implemented using hardware, software or a combination thereof and may be implemented in one or more computer systems or other processing systems. In one embodiment, the invention is directed toward one or more computer systems capable of carrying out the functionality described herein.

FIG. 1 shows a computer system 1 that includes one or more processors, such as processor 4. The one or more processors may be housed on a terminal. The processor 4 is connected to a communication infrastructure 6 (e.g., a communications bus, cross-over bar, or network). Various software embodiments are described in terms of this exemplary computer system. After reading this description, it will become apparent to a person skilled in the relevant art(s) how to implement the invention using other computer systems and/or architectures.

Computer system 1 can include a display interface 2 that forwards graphics, text, and other data from the communication infrastructure 6 (or from a frame buffer not shown) for display on the display unit 30. Computer system 1 also includes a main memory 8, preferably random access memory (RAM), and may also include a secondary memory 10. The secondary memory 10 may include, for example, a hard disk drive 12 and/or a removable storage drive 14, representing a floppy disk drive, a magnetic tape drive, an optical disk drive, etc. The removable storage drive 14 reads from and/or writes to a removable storage unit 18 in a well known manner. Removable storage unit 18, represents a floppy disk, magnetic tape, optical disk, etc., which is read by and written to removable storage drive 14. As will be appreciated, the removable storage unit 18 includes a computer usable storage medium having stored therein computer software and/or data.

In alternative embodiments, secondary memory 10 may include other similar devices for allowing computer programs or other instructions to be loaded into computer system 1. Such devices may include, for example, a removable storage unit 22 and an interface 20. Examples of such may include a program cartridge and cartridge interface (such as that found in video game devices), a removable memory chip (such as an erasable programmable read only memory (EPROM), or programmable read only memory (PROM)) and associated socket, and other removable storage units 22 and interfaces 20, which allow software and data to be transferred from the removable storage unit 22 to computer system 1.

Computer system 1 may also include a communications interface 24. Communications interface 24 allows software and data to be transferred between computer system 1 and external devices. Examples of communications interface 24 may include a modem, a network interface (such as an Ethernet card), a communications port, a Personal Computer Memory Card International Association (PCMCIA) slot and card, etc. Software and data transferred via communications interface 24 are in the form of signals 28, which may be electronic, electromagnetic, optical or other signals capable of being received by communications interface 24. These signals 28 are provided to communications interface 24 via a communications path (e.g., channel) 26. This path 26 carries signals 28 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 14, a hard disk installed in hard disk drive 12, and signals 28. These computer program products provide software to the computer system 1. The invention is directed to such computer program products.

Computer programs (also referred to as computer control logic) are stored in main memory 8 and/or secondary memory 10. Computer programs may also be received via communications interface 24. Such computer programs, when executed, enable the computer system 1 to perform the features of the present invention, as discussed herein. In particular, the computer programs, when executed, enable the processor 4 to perform the features of the present invention. Accordingly, such computer programs represent controllers of the computer system 1.

In an embodiment where the invention is implemented using software, the software may be stored in a computer program product and loaded into computer system 1 using removable storage drive 14, hard drive 12, or communications interface 24. The control logic (software), when executed by the processor 4, causes the processor 4 to perform the functions of the invention as described herein. In another embodiment, the invention is implemented primarily in hardware using, for example, hardware components, such as application specific integrated circuits (ASICs). Implementation of the hardware state machine so as to perform the functions described herein will be apparent to persons skilled in the relevant art(s).

In yet another embodiment, the invention is implemented using a combination of both hardware and software.

Figure 2:
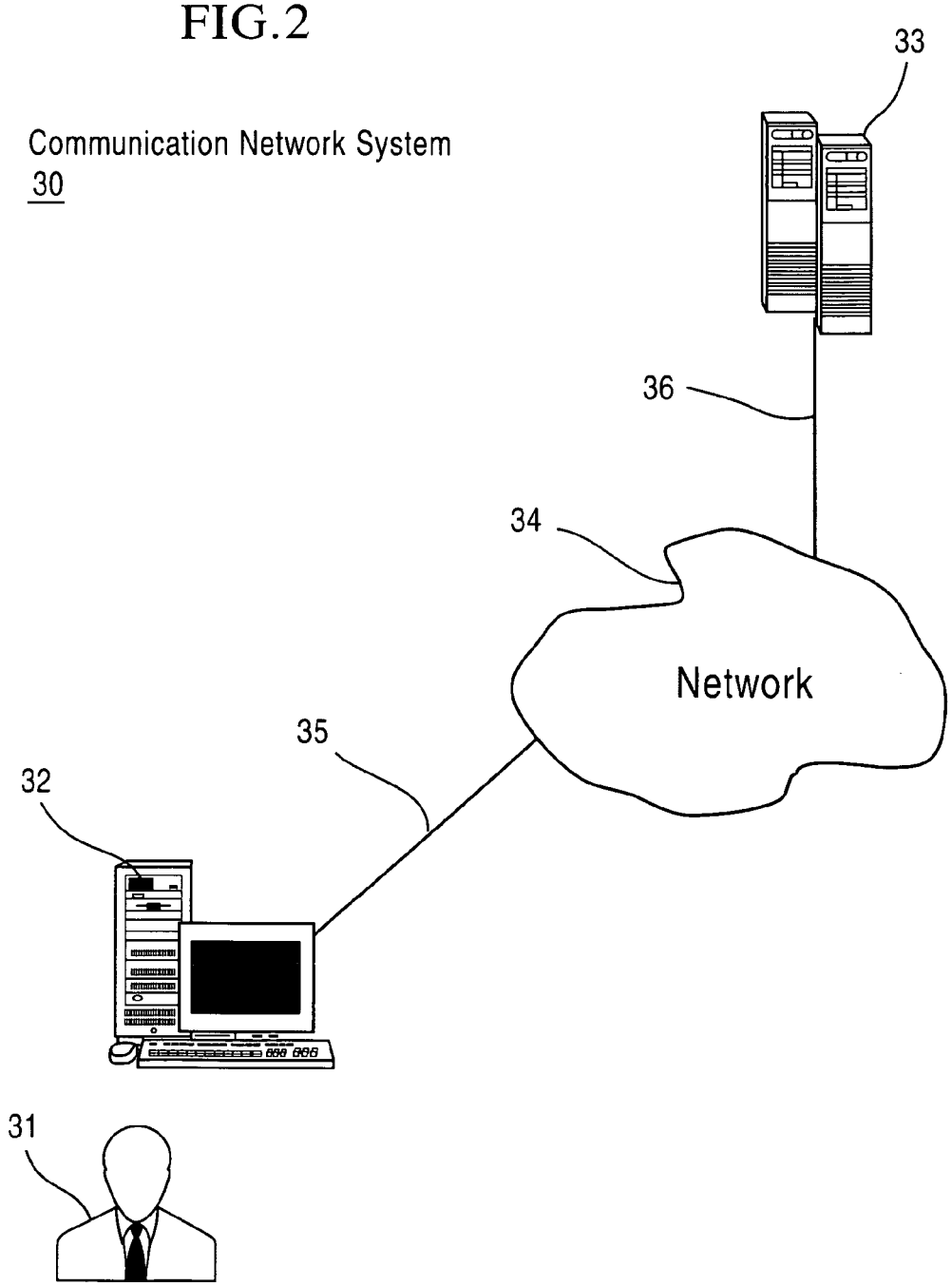
FIG. 2 presents an exemplary system diagram of various hardware components and other features in accordance with an embodiment of the present invention.

FIG. 2 shows a communication system 30 of the present invention for use with the computer system 1 of FIG. 1. The communication system 30 includes an accessor 31 (also referred to interchangeably herein as a "user") and a terminal 32. In one embodiment, data for use in the computer system 1 is, for example, input and/or accessed by the accessor 31 via the terminal 32, such as a personal computer (PC), minicomputer, mainframe computer, microcomputer, telephonic device, or wireless device, such as a hand-held wireless device coupled to a server 143, such as a PC, minicomputer, mainframe computer, microcomputer, or other device having a processor and a repository for data and/or connection to a processor and/or repository for data, via, for example, a network 34, such as the Internet or an intranet, and couplings 35, 36. The couplings 35, 36 include, for example, wired, wireless, or fiberoptic links. In another embodiment, the method and system of the present invention operate in a stand-alone environment, such as on a single terminal.

Figure 3:
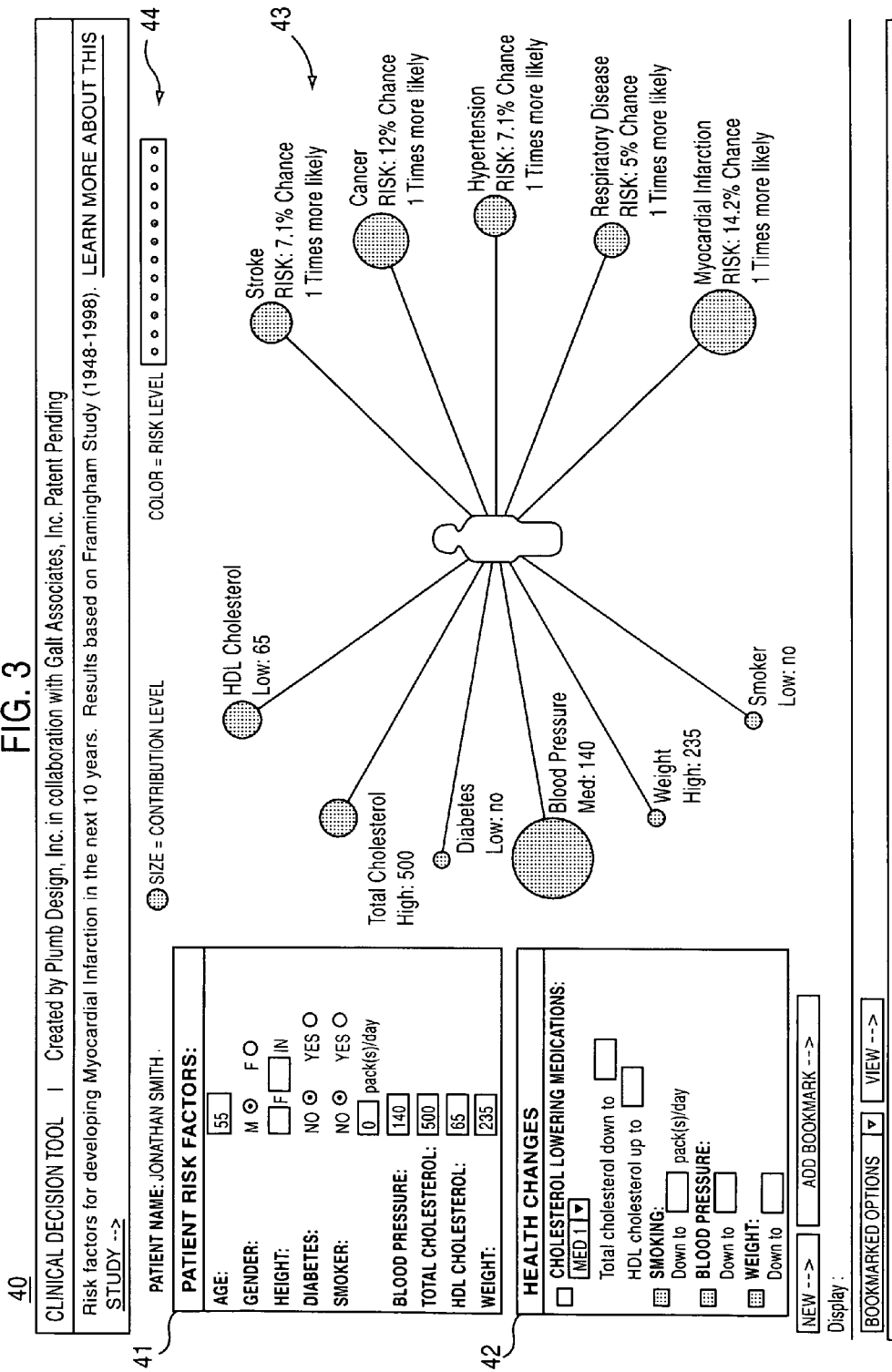
FIG. 3 illustrates one exemplary example of an overview graphic user-interface screen for use in accordance with an embodiment of the present invention.

FIG. 3 illustrates one exemplary variation of an overview graphic user-interface screen 40 for use with the computer system 1 of the present invention. The graphic user-interface screen 40 includes a Patient Risk Factors section 41, a Health Changes section 42, a Graphical Predictive Indicator section 43, and an information/reference bar 44.

The Patient Risk Factors section 41 includes a plurality of parameters related to a patient, such as the patient's age, gender, height, and weight. Furthermore, the Patient Risk Factors section 41 includes the parameters of whether the patient has diabetes or is a smoker, and information on the patient's blood pressure, total cholesterol, and high density lipoproteins (HDL) cholesterol.

Additionally, the graphic user-interface screen 40 includes a Health Changes section 42 that also has a plurality of parameters associated with any health changes and/or predictive health changes. For example, the parameters in this section can show the type of medication the patient is currently taking, changes in the smoking habits of the patient, and changes in the blood pressure and weight of the patient.

The plurality of parameters listed above are provided as examples of the exemplary embodiment of the present invention. It is understood to one skilled in the art that additional parameters may be included within the Patient Risk Factors section 41, as well as the Health Changes section 42.

The Graphical Predictive Indicator section 43 includes a graphical image showing the relationship between risk and benefit to the patient, based on the information entered for the plurality of parameters. The Graphical Predictive Indicator section 43 can illustrate information concerning the patient's health, in comparison with the predictive "RISK" information of the likelihood of a patient having a particular medical condition based on the information provided.

For example, Framingham data (more than 50 years' worth of data from the Framingham Heart Study, which has involved three generations of Framingham residents and was started by Bethesda, Md.-based National Heart, Lung, and Blood Institute) can be used to show graphically the relationship between risk and benefit of an exemplary patient, referred to on this example as Jonathan Smith. However, the present invention can incorporate any clinical and/or statistical data to show the relationship between risk and benefit of a patient, in order to facilitate clinical decisions.

Upon first entering the information in the plurality of parameters of the Patient Risk Factors section 41, the present example presents a plurality of circular indicators, interchangeably referred to herein as "bubbles," having different colors and different sizes. As shown in the indicator bar 44, the size of the bubbles can indicate the contribution level of the risk factor, and the color of the bubbles can indicate various risk levels.

In this example, the patient Jonathan Smith is a 55 years old male with no diabetes, who is a non-smoker weighing 235 pounds. Mr. Smith has a blood pressure of 140, a total cholesterol of 500, and HDL cholesterol of 65. Using these data, the computer system 1 can display a graphical image within the Graphical Predictive Indicator section 43 showing, for example, an average size blue bubble representing Mr. Smith's HDL cholesterol, which is low at 65, and a red bubble representing Mr. Smith's total cholesterol, which is high at 500.

Further, in this example, the Graphical Predictive Indicator section 43 provides information concerning the "RISK" of Mr. Smith having a particular medical or health condition. For instance, the example shows that Mr. Smith has a 7.1% chance of having a stroke, a 12% chance of having cancer, and 14.2% chance of having myocardial infraction, based on the data entered into the Patient Risk Factors section 41.

Figure 4:
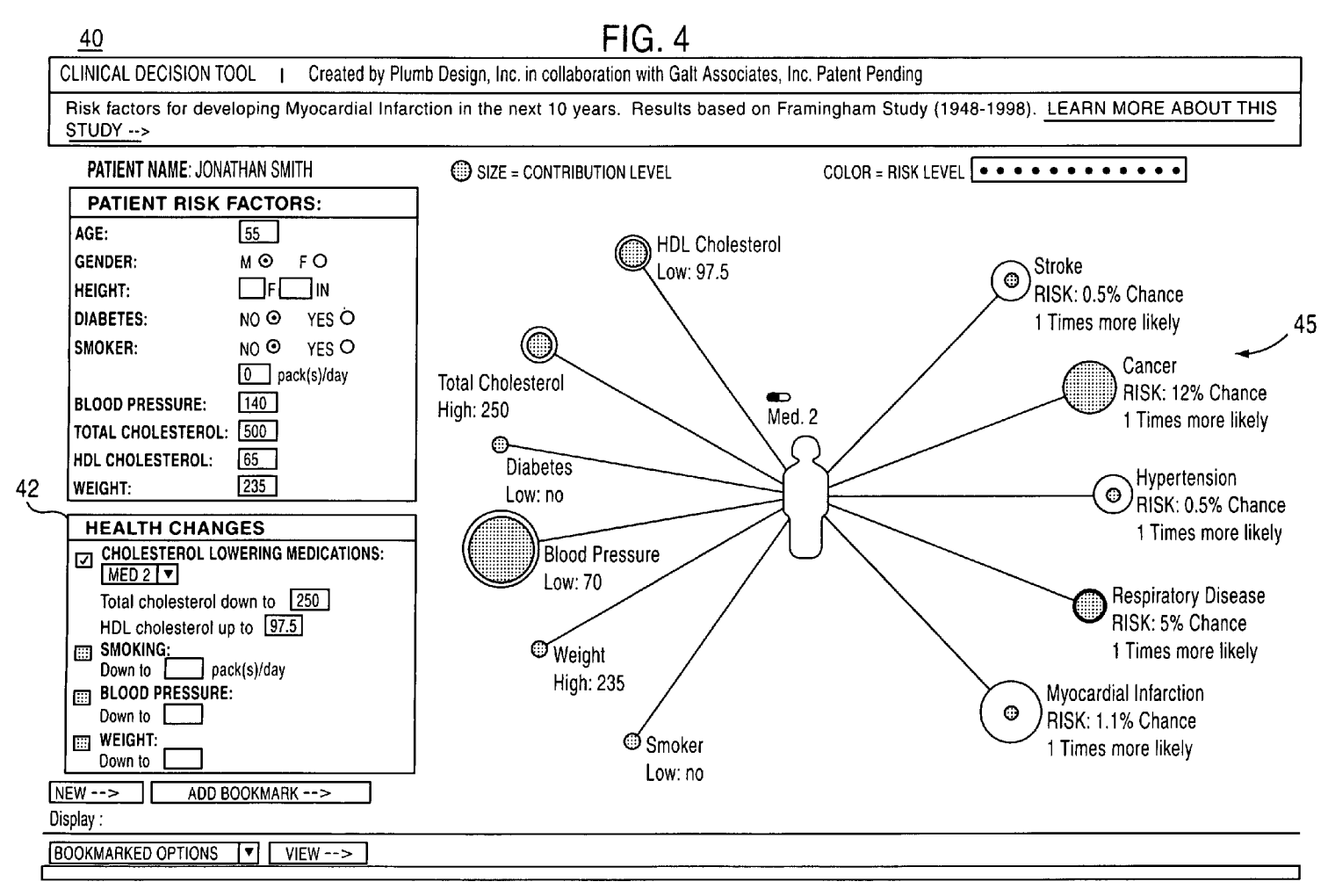

The present invention also shows changes in the Graphical Predictive Indicator section 43, when data is entered for the parameters of the Health Changes section 42. FIG. 4 shows an example of the graphic user-interface screen 40 of FIG. 3, based on the example data for Mr. Smith.

FIG. 4 also presents the results of the entry of some health changes data 42, such as if Mr. Smith takes a cholesterol lowering medication MED2, which would drop the total cholesterol down to 250, but at the same time would increase the HDL cholesterol to 97.5.

Upon entering such information, the present invention can show an updated Graphical Predictive Indicator section 45, with changes made to the information concerning the patient's health shown in comparison with the predictive "RISK" information of the likelihood of a patient having a particular medical condition, based on the additional information provided. For example, as is apparent in FIG. 4, the size of certain bubbles has decreased (e.g., previous size shown as outline only), and the colors of some bubbles have changed, reflecting changes in risk. In essence, the Graphical Predictive Indicator section can thus graphically provide information that can show the relationship between risk and benefit with taking certain drugs or the patient taking other action. Graphically, for example, the concept can be illustrated that if the patient stops smoking, the patient's cholesterol level is reduced by 20% and the risk of dying drops 10%. Similarly, a bubble may appear on the risk side that represents the additional risk conferred by the treatment itself (e.g., side effect of a drug).

Furthermore, one embodiment of the present invention can provide addition medical or health information to the user. For example, the Graphical Predictive Indicator section 43, as shown in FIG. 3, can be configured to link the user to information regarding any of the displayed health categories, such as HDL cholesterol, diabetes, stroke, cancer or myocardial infraction, by positioning the cursor to that particular category. For instance, if a user were to position the cursor to the category of "stroke" and initiate access (e.g., clicking the mouse button), then information related to the category of "stroke" would be available to the user. The information may be displayed on the display screen in text, still images, voice, or video, for example.

Figure 6:
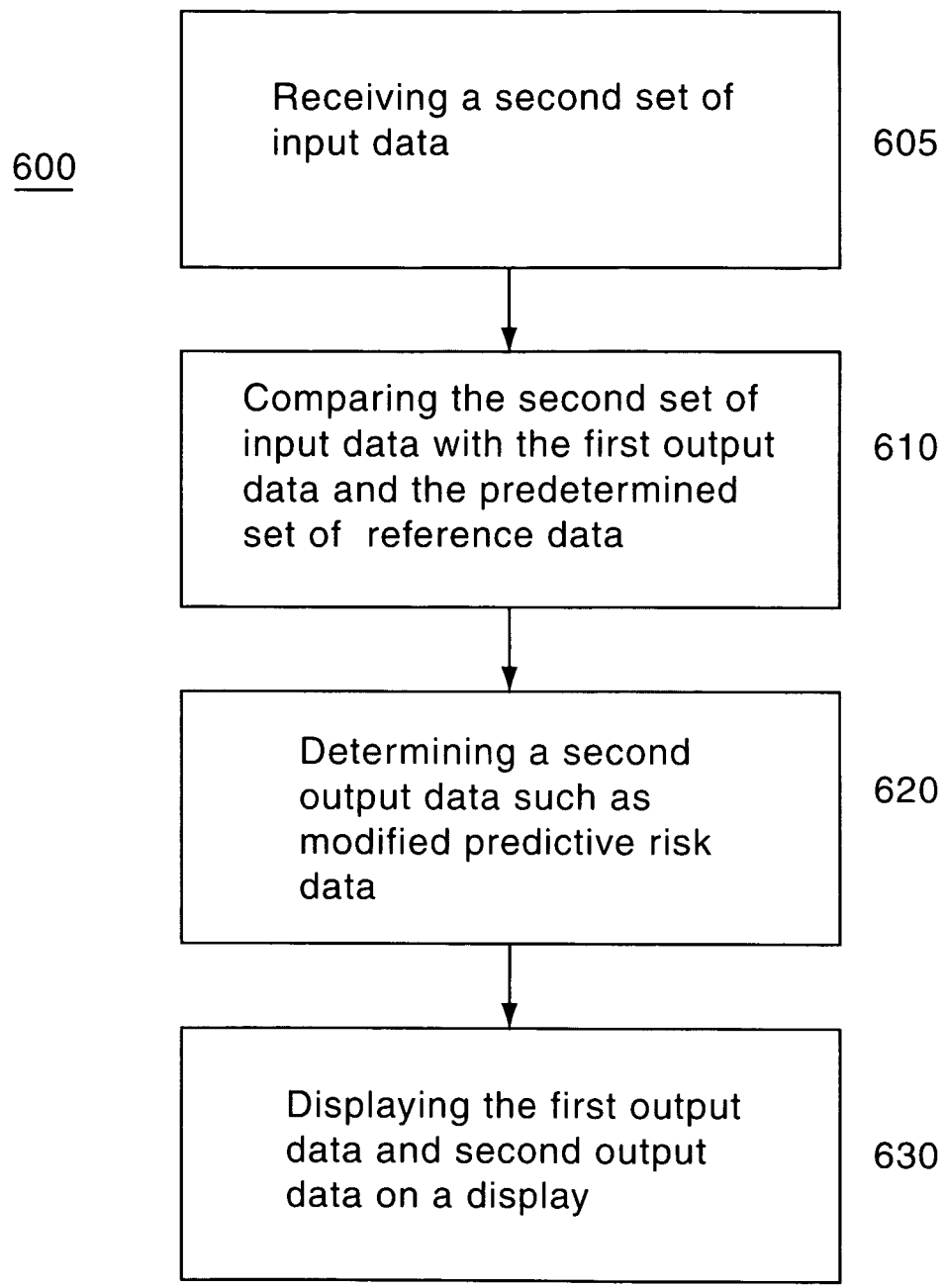
FIG. 6 illustrates the method and steps of another embodiment of the present invention.
Figure 8:
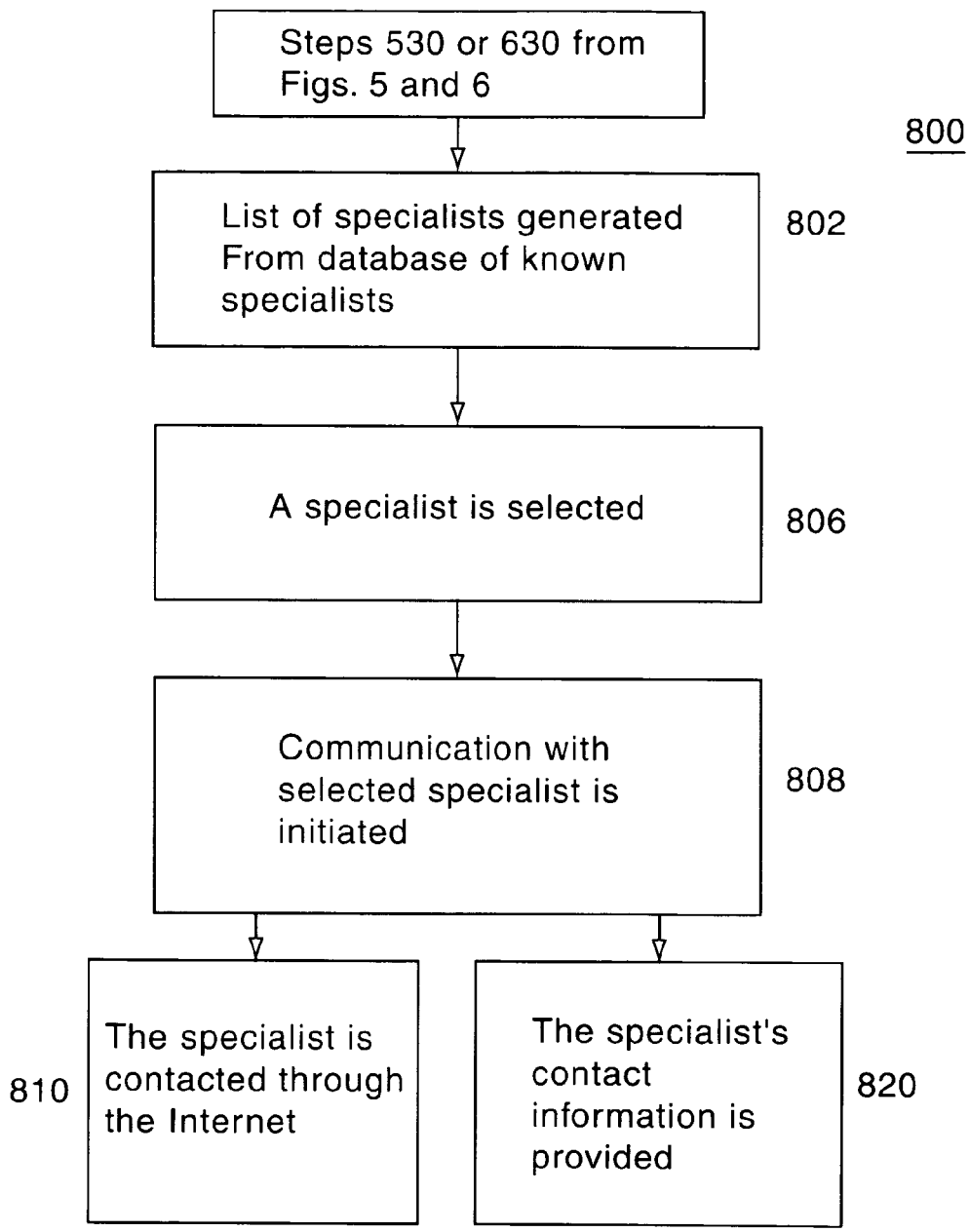
FIG. 8 illustrates the method and steps of another embodiment of the present invention.

Additionally, in one embodiment of the present invention, the computer system 1 can also be configured to connect to and communicate with another specialist, such as a physician, via the network, as further described with reference to FIG. 8. In one embodiment of the invention, as shown in FIG. 6, after such a step as displaying the first output data and second output data on a display 630, a list of specialists may be generated from a known database 802, as shown in FIG. 8.

The known database could be locally stored and retrieved, or the database could be retrieved across a network, for example. Next, a specialist is selected 806, either through user selection or selection by the system. The system or user then initiates communication with that specialist 808. In one embodiment, the system initiates communication via the Internet to contact the specialist 810. In another embodiment, the system initiates communication by providing the specialist's contact information 820, retrieved from the database 804. In yet another embodiment, rather than connecting and communicating with another specialist, the present invention directs the user to an additional source of information, such as an Internet site or an article in a magazine or medical journal.

Figure 5:
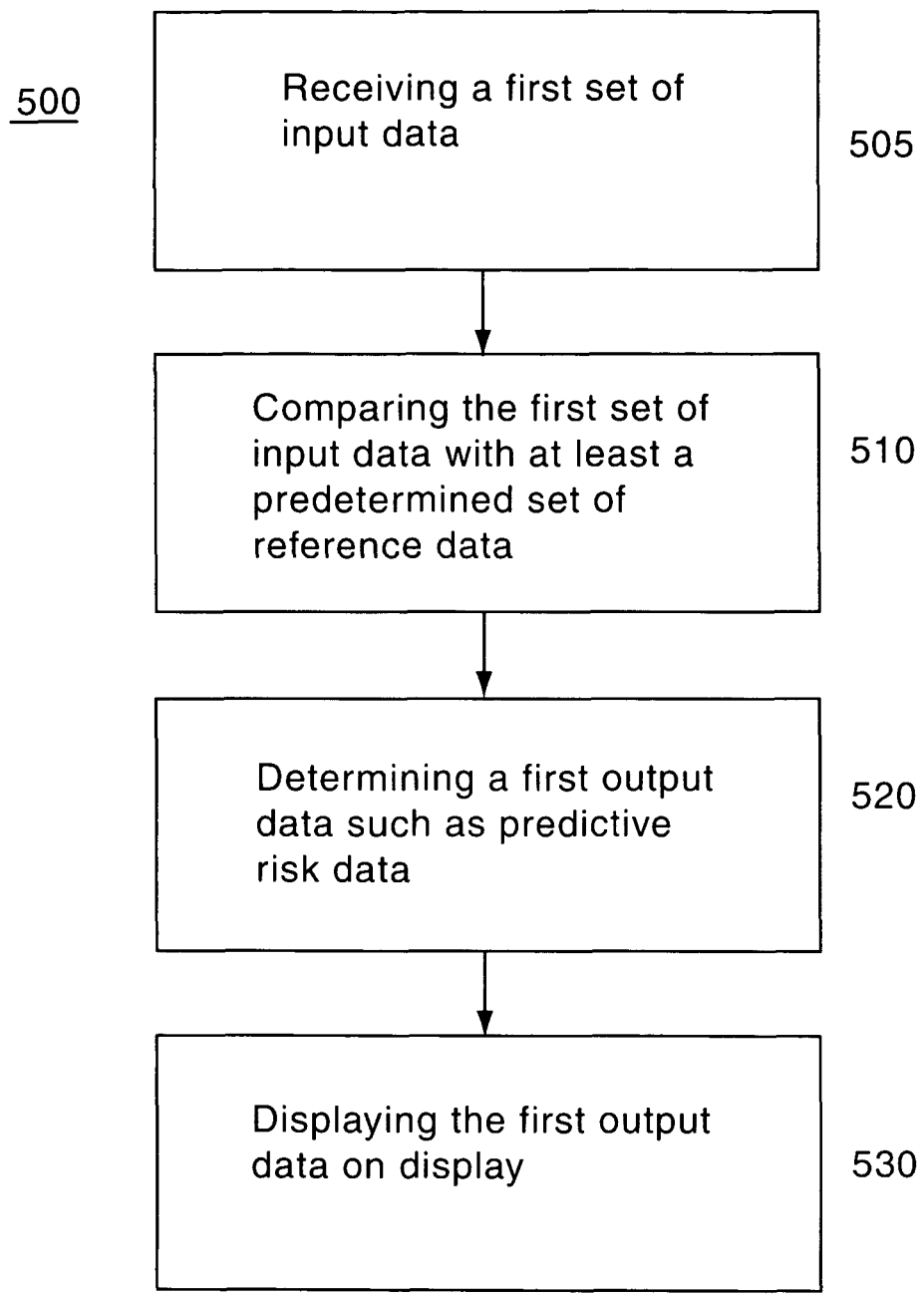
FIG. 5 illustrates the method and steps of one embodiment of the present invention.

FIG. 5 illustrates the method and steps of one embodiment of the present invention 500. In step 505, a first set of input data is received. For example, the first set of input data received can be a plurality of parameters entered into the patient risk factors section 41, as shown in FIG. 3. The first set of input data can include data such as age, gender, height, presence of diabetes, whether the patient is a smoker, blood pressure, total cholesterol, HDL cholesterol and weight. Other personal and clinical based information may also be included in the first set of input data.

Once the first set of input data is entered and received in the system, in step 510, the first set of input data is compared with at least a predetermined set of reference data, such as the Framingham data. For instance, the present invention can store a set of reference data, such as the Framingham data, in a storage medium, and upon receiving the first set of input data, the present invention compares the first set of input data with the stored Framingham data.

Thereafter, in step 520 of the present invention, a first output data is determined. For example, in step 520, the output data can be determined, including the Graphical Predictive Indicator section to be displayed with a graphical image showing the relationship between risk and benefit of the patient, based on the information entered into the plurality of parameters. In addition, the first output data can include information concerning the patient's health, in comparison with the predictive "RISK" information of the likelihood of a patient having a particular medical condition based on the information provided.

Once the first output data is determined, in step 530, the first output data is displayed on a display or otherwise presented. For example, the present example shows a plurality of different circular indicators, interchangeably referred to herein as "bubbles," having different colors and different sizes. The circular indicators are part of the display showing the "RISK" of a particular case/patient having a particular medical or health condition. For instance, the example of FIG. 3 shows that Mr. Smith has a 7.1% chance of having a stroke, a 12% chance of having cancer, and 14.2% chance of having myocardial infraction, based on the data entered into the Patient Risk Factors section 41.

FIG. 6 illustrates the method and steps of another embodiment of the present invention 600. In step 605, a second set of input data are received. For example, the second set of input data received can include a plurality of parameters entered into the Health Changes section 42 of FIG. 3. The second set of input data can include data such as cholesterol lowering medications, smoking changes, blood pressure changes, and weight changes. Other personal and clinical based information may also be included in the second set of input data.

Once the second set of input data is entered and received in the system, in step 610 the second set of input data are compared with the first set of output data, and with at least a predetermined set of reference data, such as the Framingham data. For instance, upon receiving the second set of input data, the present invention compares the second set of input data with the age, gender, height, diabetes status, smoking status, blood pressure, total cholesterol, HDL cholesterol and weight of the individual patient, and with the stored Framingham data.

Thereafter, in step 620 of the present invention, a second output data is determined. For example, in step 620, the second output data can be determined including changes in the Graphical Predictive Indicator section 43, as shown in FIG. 3, when data is entered in the parameters of the Health Changes section 42 of FIG. 3. FIG. 4 shows an example of the second output data, based on the example patient of Mr. Smith. FIG. 4 also presents an example of the second output data results for the entry of some health changes data, such as if Mr. Smith takes a cholesterol lowering medication MED2, which would drop the total cholesterol down to 250, but at the same time increase the HDL cholesterol to 97.5.

Once the second output data is determined, in step 630, the second output data are presented, along with the first output data. For example, in FIG. 4, the present example shows a plurality of different circular indicators, interchangeably referred to herein as "bubbles," having different colors and different sizes. In particular, as shown in FIG. 4, the present invention can display an updated Graphical Predictive Indicator section 45, with changes made to the information concerning the patient's health shown in comparison with the predictive "RISK" information of the likelihood of a patient having a particular medical condition, based on the additional information provided.

Figure 7:
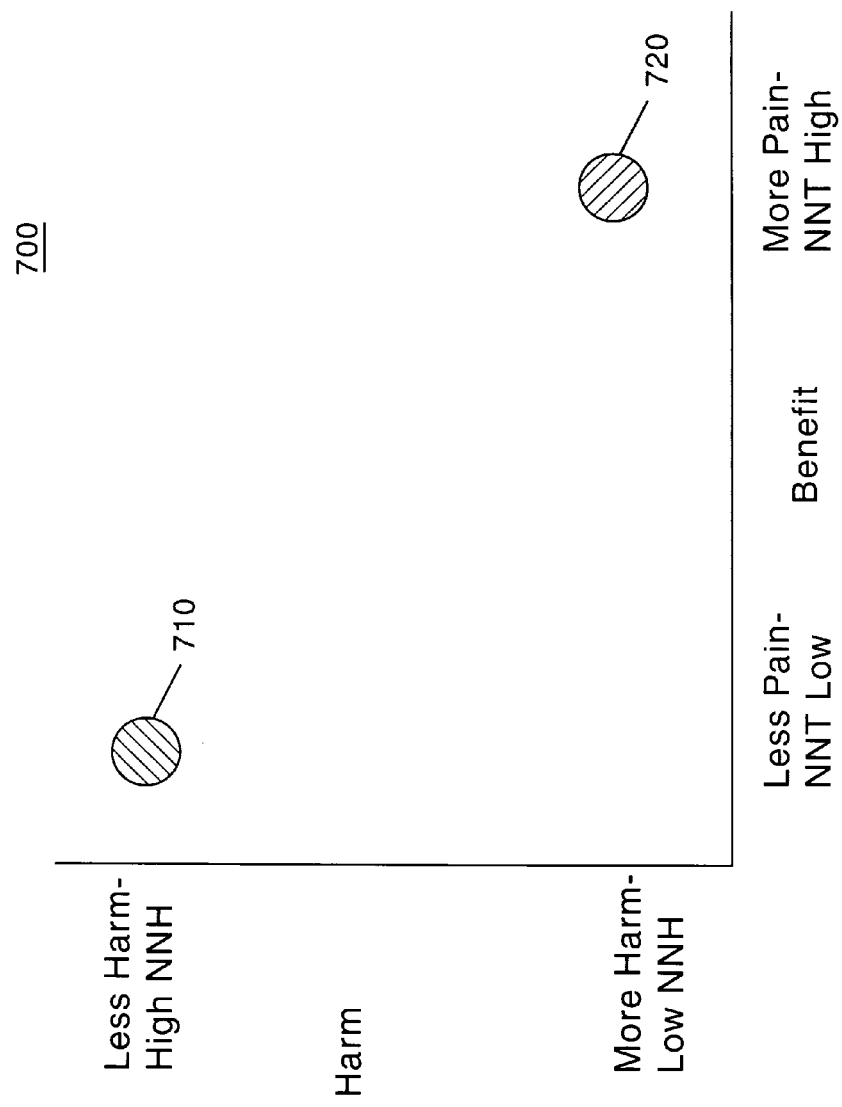
FIG. 7 illustrates an example of a screen generated in one embodiment of the present invention, based on harm/benefit ratios.

One embodiment of the present invention graphically displays benefit/harm ratios, as shown in FIG. 7. FIG. 700 represents a graphical display of the potential benefits and risks of a course of therapy. The X-axis represents the "NNT", or "Number Needed to Treat," increasing from low to high. The NNT value represents the number of patients that must be treated with a specific course of therapy in order to prevent one adverse outcome. Generally, a lower NNT value corresponds to a higher benefit associated with the course of therapy. The Y-axis represents the "NNH", or the "Number Needed to Harm," increasing from low to high. Similarly to the NNT, the NNH number represents the number of patients that must be treated with a specific course of therapy in order to cause one harmful outcome. Generally, a higher NNH value corresponds to a less harmful course of therapy.

For example, the point 710 is located on the graph in an area corresponding to a high NNH and a low NNT. The course of therapy represented by point 710 on the graph will thus have a high likelihood of benefit, and a low likelihood of harm. As a further example, the point 720 is located on the graph in an area corresponding to a low NNH and a high NNT. Thus, the course of therapy represented by point 720 on the graph will have a low likelihood of benefit, and a high likelihood of pain. In one embodiment of the present invention, multiple courses of therapy may be displayed on a single graph, creating a graphical indicator of the relative risks and benefits associated with each course of therapy.

In another embodiment of the present invention, the computer system of the present invention combines information provided from the plurality of parameters in the Patient Risk Factors, with previously stored information about known risk factors that increase the likelihood of a particular affliction. For example, parameters such as whether the patient is a smoker, or a diabetic, the patient's cholesterol levels, and the patient's family history, are combined with the known risk factors of existing valvular disease, viral infection, alcohol use, thiamine deficiencies, and myopathies, to calculate and illustrate the increasing risk of such symptoms as elevated blood pressure, which can in turn lead to coronary arthrosclerosis, stroke, renal failure, myocardial infarction and congestive heart failure.

In another embodiment of the present invention, the presence of one medical condition affects the calculation of the risk of other related medical conditions. An exemplary patient, referred to here as Jane Jones, has the preexisting medical condition of diabetes. Due to the presence of this condition, the Graphical Predictive Indicator will display predictive "RISK" information of related medical conditions, such as depressive disorder, chronic heart disease, osteoarthrosis, metabolic disorders, retinal disorders, renal failure, anemias, cataracts and hypertension, based on the presence of Jane Jones's diabetes.

In an embodiment where the invention is implemented using software, the software may be stored in a computer program product and loaded into computer system using removable storage drive, hard drive, servers, wireless transmitters and receivers, mobile communication devices and/or communications interface. The control logic (software), when executed by the processor, causes the processor to perform the functions of the invention as described herein. In another embodiment, the invention is implemented primarily in hardware using, for example, hardware components, such as application specific integrated circuits (ASICs). Implementation of the hardware state machine so as to perform the functions described herein will be apparent to persons skilled in the relevant art(s).

In yet another embodiment, the invention is implemented using a combination of both hardware and software.

Example embodiments of the present invention have now been described in accordance with the above advantages. It will be appreciated that these examples are merely illustrative of the invention. Many variations and modifications will be apparent to those skilled in the art, such as wireless communications using a mobile phone or a PDA.

The invention claimed is:

1. Computer hardware storage media having computer-executable instructions tangibly embodied thereon that, when executed by a computing device, cause the computing device to perform a method for providing information for facilitating health care and clinical decisions, the method comprising:
   receiving a first set of input data corresponding to patient information of an individual patient, wherein the first set of input data comprises blood pressure and total cholesterol of the individual patient at a first point in time;
   comparing the first set of input data with at least a predetermined set of reference data relating risk factors to heart conditions;
   determining a first set of output data comprising risk factors of the individual patient that contribute to the individual patient developing one or more heart conditions, and further determining a contribution level of each of the determined risk factors to the one or more heart conditions based on the comparing the first set of input data with the at least the predetermined set of reference data relating risk factors to heart conditions;
   presenting the first set of output data comprising a graphical indicator of the each of the determined risk factors, the each of the determined risk factors being presented as the graphical indicator, wherein a size of the graphical indicator is based on the contribution level of the each of the determined risk factors, wherein a larger size indicates a higher contribution level;
   receiving a second set of input data specifying new patient information of the individual patient, wherein the second set of input data is associated with a potential treatment that has not yet been initiated, and wherein the second set of input data comprises medication changes, smoking changes, blood pressure changes, and weight changes;
   comparing the second set of input data with the first set of output data and the at least the predetermined set of reference data relating risk factors to heart conditions;
   determining a second set of output data comprising revised risk factors of the individual patient, and further determining a revised contribution level of each of the revised risk factors to the one or more heart conditions based on the comparing the second set of input data with the first set of output data and the at least the predetermined set of reference data relating risk factors to heart conditions; and
   presenting the second set of output data along with the first set of output data to graphically show a relationship between a potential risk and a potential benefit associated with the potential treatment, wherein presenting the second set of output data comprises presenting a revised graphical indicator of the each of the revised risk factors, a revised size of the revised graphical indicator being based on the revised contribution level of the each of the revised risk factors to the one or more heart conditions, and wherein a difference between the size of the graphical indicator of the each of the determined risk factors and the revised size of the revised graphical indicator of the each of the revised risk factors indicates a change in the contribution level of the each of the determined risk factors, the change in the contribution level of the each of the determined risk factors being associated with the potential treatment.

2. The computer hardware storage media of claim 1, wherein the first set of input data further comprises at least one selected from a group consisting of the patient's age, gender, height, weight, smoking status, diabetic status, and HDL cholesterol.

3. The computer hardware storage media of claim 1, wherein the predetermined set of reference data includes Framingham data.

4. The computer hardware storage media of claim 1, wherein displaying the first set of output data includes displaying a plurality of circular indicators corresponding to patient risk factors.

5. The computer hardware storage media of claim 4, wherein the plurality of circular indicators have a plurality of sizes, and wherein a size of one of the plurality of circular indicators indicates the contribution of the patient risk factor represented by the one of the plurality of circular indicators.

6. The computer hardware storage media of claim 5, wherein each of the plurality of circular indicators is one of a plurality of colors, and wherein the color of each of the plurality of circular indicators corresponds to risk level of the patient risk factor represented by the one circular indicator.

7. The computer hardware storage media of claim 1, further comprising:
   generating a list of specialists;
   selecting one of the specialists from the list; and
   initiating communication with the selected specialist.

8. The computer hardware storage media of claim 1, further comprising:
   providing direction to a secondary information source.

9. The computer hardware storage media of claim 8, wherein the secondary information source is a web site.

10. The computer hardware storage media of claim 1, further comprising:

generating a list of specialists;
selecting one of the specialists from the list; and
initiating communication with the selected specialist.

11. A system for electronically providing information for facilitating health care and clinical decisions, comprising:
a hardware processor; and
a repository accessible by the hardware processor;
wherein a first set of input data specifying patient information associated with a patient and a second set of input data specifying potential changes in the patient information, including medication changes, smoking changes, blood pressure changes, and weight changes, are received and stored in the repository, wherein the patient information corresponds to a current condition of the patient and the potential changes in patient information correspond to a potential future condition of the patient, the potential future condition of the patient being associated with a potential course of treatment that has not yet been initiated;
wherein the first set of input data is compared with at least a predetermined set of reference data relating risk factors to strokes via the processor;
wherein a first set of output data and a second set of output data are identified via the processor, the first set of output data comprising risk factors of the patient that contribute to the patient developing strokes, a contribution level of each of the risk factors determined based on the comparing of the first set of input data and the at least the predetermined set of reference data relating risk factors to strokes, and the second set of output data comprising revised risk factors of the patient that contribute to the patient developing a stroke, the second set of output data based on comparing the second set of input data to the first set of output data and the predetermined set of reference data relating risk factors to strokes;
wherein a revised contribution level of each of the revised risk factors is determined via the processor, the revised contribution level based on the comparing the second set of input data to the first set of output data and the predetermined set of reference data relating risk factors to strokes;
wherein an extent of difference between the contribution level of the each of the determined risk factors and the revised contribution level of the each of the revised risk factors is determined via the processor; and
wherein the first set of output data is presented along with the second set of output data via a graphical user interface to graphically show a potential benefit and risk associated with the potential course of treatment, wherein presenting the first set of output data includes presenting graphical indicators of the determined risk factors, the each of the determined risk factors presented as a graphical indicator, wherein a size of the graphical indicator is based on the contribution level of the each of the determined risk factors, wherein a larger size indicates a higher contribution level.

12. The system of claim 11, wherein the processor is housed on a terminal.

13. The system of claim 11, wherein a terminal is selected from a group consisting of a personal computer, a minicomputer, a main frame computer, a microcomputer, a hand held device, and a telephonic device.

14. The system of claim 11, wherein the processor is housed on a server.

15. The system of claim 14, wherein the server is selected from a group consisting of a personal computer, a minicomputer, a microcomputer, and a main frame computer.

16. The system of claim 14, wherein the server is coupled to a network.

17. The system of claim 16, wherein input is received via the network.

18. The system of claim 16, wherein the network is the Internet.

19. The system of claim 16, wherein the server is coupled to the network via a coupling.

20. The system of claim 19, wherein the coupling is selected from a group consisting of a wired connection, a wireless connection, and a fiberoptic connection.

21. The system of claim 11, wherein the repository is housed on a server.

22. The system of claim 21, wherein the server is coupled to a network.

23. Computer hardware storage media having computer-executable instructions tangibly embodied thereon that, when executed by a computing device, cause the computing device to perform a method for providing information for facilitating health care and clinical decisions, the method comprising:
receiving a first set of input data corresponding to patient information associated with a patient, wherein the first set of input data comprises weight, blood pressure, HDL cholesterol, and total cholesterol of the patient at a first point in time;
comparing the first set of input data with a predetermined set of reference data relating to risk factors of strokes;
determining a first set of output data comprising risk factors of the patient that contribute to the patient developing strokes, and further determining a contribution level of each of the determined risk factors based on the comparing the first set of input data with the predetermined set of reference data relating to risk factors of strokes;
presenting the first set of output data comprising graphical indicators of the determined risk factors, the each of the determined risk factors presented as a graphical indicator, wherein a size of the graphical indicator is based on the contribution level of the each of the determined risk factors, wherein a larger size indicates a higher contribution level;
receiving a second set of input data corresponding to revised patient information, wherein the second set of input data comprises medication changes, smoking changes, blood pressure changes, and weight changes;
comparing the second set of input data with the first set of output data and with the predetermined set of reference data relating to risk factors of strokes;
determining a second set of output data comprising revised risk factors of the patient that contribute to the patient developing a stroke, and further determining a revised contribution level of the each of the revised risk factors determined based on the comparing the second set of input data with the first set of output data and with the predetermined set of reference data relating to risk factors of strokes;
determining an extent of difference between the contribution level of the each of the determined risk factors and the revised contribution level of the each of the revised risk factors;
presenting the second set of output data comprising revised graphical indicators of the revised risk factors along with the first set of output data to graphically show a relationship between risk and benefit associated with the medication changes, smoking changes, blood pressure changes, and weight changes; and presenting potential benefits and risks of a potential course of therapy.

* * * * *